(12) United States Patent
Vaughn et al.

(10) Patent No.: US 7,722,878 B2
(45) Date of Patent: May 25, 2010

(54) PRRSV SUBUNIT VACCINES

(75) Inventors: Eric M. Vaughn, Ames, IA (US);
Richard Stammer, Ames, IA (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 672 days.

(21) Appl. No.: 11/154,617

(22) Filed: Jun. 16, 2005

(65) Prior Publication Data

US 2008/0038293 A1    Feb. 14, 2008

Related U.S. Application Data

(60) Provisional application No. 60/581,350, filed on Jun. 17, 2004.

(51) Int. Cl.
*A61K 39/12*    (2006.01)
(52) U.S. Cl. .................................. 424/186.1; 435/6
(58) Field of Classification Search .............. 424/186.1, 424/204.1
See application file for complete search history.

(56) References Cited

U.S. PATENT DOCUMENTS 6,773,908 B1 *  8/2004  Paul et al. ................. 435/235.1
2002/0012670 A1 *  1/2002  Elbers et al. ............. 424/204.1

OTHER PUBLICATIONS

Barfoed et al, Vaccine, 2004, vol. 22, pp. 3628-3641 (available online Apr. 10, 2004).*
Johnston et al, Vaccine, Jun. 1997;15(8):808-809.*

* cited by examiner

*Primary Examiner*—Ali R. Salimi
(74) *Attorney, Agent, or Firm*—Michael P. Morris; Mary-Ellen M. Devlin; Joyce L. Morrison

(57) ABSTRACT

Vaccines effective against PRRSV include at least one portion of PRRSV ORF1. Such vaccines, upon administration, provoke an immune response in PRRSV-susceptible animals. Moreover, compositions in accordance with the present invention provide immune response up to and including protective immunity against PRRSV as well as reduce the severity of PRRSV and/or incidence of PRRSV. Selected portions of ORF1 can be used singularly, in combination with one another, in combination with other PRRSV ORFs, and in combination with other PRRSV vaccines.

14 Claims, No Drawings

SEQUENCE LISTING

```
<160> NUMBER OF SEQ ID NOS: 14

<210> SEQ ID NO 1
<211> LENGTH: 15411
<212> TYPE: DNA
<213> ORGANISM: Porcine reproductive and respiratory syndrome virus

<400> SEQUENCE: 1
atgacgtata ggtgttggct ctatgccttg gcatttgtat tgtcaggagc tgtgaccatt      60
ggcacagccc aaaacttgct gcacagaaac acccttctgt gatagcctcc ttcagggag      120 cttagggttt gtccctagca ccttgcttcc ggagttgcac tgctttacgg tctctccacc     180
cctttaacca tgtctgggat acttgatcgg tgcacgtgta cccccaatgc cagggtgttt     240
atggcggagg gccaagtcta ctgcacacga tgcctcagtg cacggtctct ccttcccctg     300
aacctccaag tttctgagct cggggtgcta ggcctattct acaggcccga agagccactc     360
cggtggacgt tgccacgtgc attccccact gttgagtgct ccccgccgg ggcctgctgg      420 cttctgcaa tctttccaat cgcacgaatg accagtggaa acctgaactt ccaacaaaga     480
atggtacggg tcgcagctga gctttacaga gccggccagc tcacccctgc agtcttgaag     540
gctctacaag tttatgaacg gggttgccgc tggtacccca ttgttggacc tgtccctgga     600
gtggccgttt tcgccaattc cctacatgtg agtgataaac ctttcccggg agcaactcac     660
gtgttgacca acctgccgct cccgcagaga cccaagcctg aagactttg ccccttgag      720 tgtgctatgg ctactgtcta tgacattggt catgacgccg tcatgtatgt ggccgaaagg     780
aaagtctcct gggcccctcg tggcgggat gaagtgaaat ttgaagctgt ccccggggag     840
ttgaagttga ttgcgaaccg gctccgcacc tccttcccgc cccaccacac agtggacatg     900
tctaagttcg ccttcacagc ccctgggtgt ggtgttctta tgcgggtcga acgccaacac     960
ggctgccttc ccgctgacac tgtccctgaa ggcaactgct ggtggagctt gtttgacttg    1020
cttccactgg aagttcagaa caaagaaatt cgccatgcta accaatttgg ctaccagacc    1080
aagcatggtg tctctggcaa gtacctacag cggaggctgc aagttaatgg tctccgagca    1140
gtaactgacc taaacggacc tatcgtcgta cagtacttct ccgttaagga gagttggatc    1200
cgccatttga aactggcggg agaacccagc tactctgggt tgaggaccct cctcagaata    1260
agggttgagc ctaacacgtc gccattggct gacaaggaag aaaaaatttt ccggtttggc    1320
agtcacaagt ggtacgcgc tggaaagaga gcaagaaaag cacgctcttg tgcgactgct    1380
acagtcgctg gccgcgcttt gtccgttcgt gaaacccggc aggccaagga gcacgaggtt    1440
gccggcgcca acaaggctga gcacctcaaa cactactccc cgcctgccga agggaattgt    1500
ggttggcact gcatttccgc catcgccaac cggatggtga attccaaatt tgaaaccacc    1560
```

-continued

```
cttcccgaaa gagtgagacc tccagatgac tgggctactg acgaggatct tgtgaatgcc   1620
atccaaatcc tcagactccc tgcggcctta gacaggaacg gtgcttgtac tagcgccaag   1680
tacgtactta agctggaagg tgagcattgg actgtcactg tgaccctgg gatgtccct    1740
tctttgctcc ctcttgaatg tgttcagggc tgttgtgggc acaagggcgg tcttggttcc   1800
ccagatgcag tcgaggtctc cggatttgac cctgcctgcc ttgaccggct ggctgaggtg   1860
atgcacctgc ctagcagtgc tatcccagcc gctctggccg aaatgtctgg cgattccgat   1920
cgttcggctt ctccggtcac caccgtgtgg actgtttcgc agttctttgc ccgtcacagc   1980
ggagggaatc accctgacca agtgcgctta gggaaaatta tcagcctttg tcaggtgatt   2040
gaggactgct gctgttccca gaacaaaacc aaccgggtca ccccggagga ggtcgcagca   2100
aagattgacc tgtacctccg tggtgcaaca aatcttgaag aatgcttggc caggcttgag   2160
aaagcgcgcc cgccacgcgt aatcgacacc tcctttgatt gggatgttgt gctccctggg   2220
gttgaggcgg caacccagac gatcaagctg ccccaggtca accagtgtcg tgctctggtc   2280
cctgttgtga ctcaaaagtc cttggacaac aactcggtcc ccctgaccgc cttttcactg   2340
gctaactact actaccgtgc gcaaggtgac gaagttcgtc accgtgaaag actaaccgcc   2400
gtgctctcca agttggaaaa ggttgttcga gaagaatatg gctcatgcc aaccgagcct    2460
ggtccacggc ccacactgcc acgcgggctc gacgaactca agaccagat ggaggaggac    2520
ttgctgaaac tggctaacgc ccagacgact tcggacatga tggcctgggc agtcgagcag   2580
gttgacctaa aaacttgggt caagaactac ccgcggtgga caccaccacc ccctccgcca   2640
aaagttcagc ctcgaaaaac gaagcctgtc aagagcttgc cggagagaaa gcctgtcccc   2700
gccccgcgca ggaaggttgg gtccgattgt ggcagcccgg tttcattagg cggcgatgtc   2760
cctaacagtt gggaagattt ggctgttagt agccccttg atctcccgac cccacctgag    2820
ccggcaacac cttcaagtga gctggtgatt gtgtcctcac cgcaatgcat cttcaggccg   2880
gcgacaccct tgagtgagcc ggctccaatt cccgcacctc gcggaactgt gtctcgaccg   2940
gtgacaccct tgagtgagcc gatccctgtg cccgcaccgc ggcgtaagtt tcagcaggtg   3000
aaaagattga gttcggcggc ggcaatccca ccgtaccagg acgagcccct ggatttgtct   3060
gcttcctcac agactgaata tgaggcctct cccccagcac cgccgcagag cggggggcgtt   3120
ctgggagtag aggggcatga agctgaggaa accctgagtg aaatctcgga catgtcgggt   3180
aacattaaac ctgcgtccgt gtcatcaagc agctccttgt ccagcgtgag aatcacacgc   3240
ccaaaatact cagctcaagc catcatcgac tcgggcgggc cctgcagtgg gcatctccaa   3300
gaggtaaagg aaacatgcct tagtgtcatg cgcgaggcat gtgatgcgac taagcttgat   3360
gaccctgcta cgcaggaatg gctttctcgc atgtgggatc gggtggacat gctgacttgg   3420
cgcaacacgt ctgtttacca ggcgatttgc accttagatg gcaggttaaa gttcctccca   3480
aaaatgatac tcgagacacc gccgccctat ccgtgtgagt ttgtgatgat gcctcacacg   3540
cctgcacctt ccgtaggtgc ggagagcgac cttaccattg gctcagttgc tactgaagat   3600
gttccacgca tcctcgagaa aatagaaaat gtcggcgaga tggccaacca gggacccttg   3660
gccttctccg aggataaacc ggtagatgac caacttgtca acgaccccg gatatcgtcg   3720
cggaggcctg acgagagcac atcagctccg tccgcaggca caggtggcgc cggctctttt   3780
accgatttgc cgccttcaga tggcgcggat gcggacgggg ggggccgtt tcggacggta    3840
aaaagaaaag ctgaaaggct cttttgaccaa ctgagccgtc aggttttga cctcgtctcc    3900
catctccctg ttttcttctc acgccttttc taccctggcg gtggttattc tccgggtgat   3960
```

```
tggggttttg cagcttttac tctattgtgc ctcttttat gttacagtta cccagccttt      4020
ggtattgctc ccctcttggg tgtgttttct gggtcttctc ggcgcgttcg aatgggggtt      4080
tttggctgct ggttggcttt tgctgttggt ctgttcaagc ctgtgtccga cccagtcggc      4140
gctgcttgtg agtttgactc gccagagtgt agaaacatcc ttcattcttt tgagcttctc      4200
aaaccttggg accctgttcg cagccttgtt gtgggccccg tcggtctcgg tcttgccatt      4260
cttggcaggt tactgggcgg ggcacgctgc atctggcact ttttgcttag gcttggcatt      4320
gttgcagact gtatcttggc tggagcttac gtgcttctc aaggtaggtg taaaaagtgc      4380
tggggatctt gtataagaac tgctcctaat gaggtcgctt ttaacgtgtt tccttcaca      4440
cgtgcgacca ggtcgtcact tatcgacctg tgcgatcggt tttgtgcgcc aaaaggaatg      4500
gaccccattt ttctcgccac tgggtggcgc gggtgctggg ccggccgaag ccccattgag      4560
caaccctctg aaaacccat cgcgtttgcc caattggatg aaaagaagat tacggctagg      4620
actgtggtcg cccagcctta tgaccccaac caagccgtaa agtgcttgcg ggtattgcag      4680
tcgggtgggg cgatggtggc taaggcggtc ccaaaagtgg tcaaggtttc cgctgttcca      4740
ttccgagccc ccttctttcc cactggagtg aaagttgacc ctgattgcag ggtcgtggtt      4800
gaccctgaca ctttcactgc agctctccgg tctggctact ccaccacaaa cctcgtcctt      4860
ggtgtagggg actttgccca gctgaatgga ttaaaaatca ggcaaatttc caagccttca      4920
gggggaggcc cacatctcat ggctgccctg catgttgcct gctcgatggc tctgcacatg      4980
cttgctggga tttatgtgac tgcggtgggt tcttgcggca ccggcaccaa cgacccgtgg      5040
tgcgctaacc cgtttgccgt ccctggctac ggacctggct ctctctgcac gtccaggttg      5100
tgcatttccc aacacggcct taccctgccc ttgacagcac ttgtggcggg attcggtatt      5160
caagaaattg ccttggtcgt tttgattttt gtttccatcg gaggcatggc tcataggttg      5220
agctgtaagg ctgacatgct gtgtgttttg cttgcaattg ccagctatgt ttgggtacct      5280
cttacctggt tgctttgtgt gtttccttgc tggttgcgct gttttctctt gcacccctc      5340
accatcctat ggttggtgtt tttcttgatt tctgtgaata tgccttcagg aatcttggcc      5400
atggtgttgt tggtttctct ttggcttctt ggtcgttata ctaatgttgc tggccttgtc      5460
accccctacg acattcatca ttacaccagt ggccccgcg tgttgccgc cttggctacc      5520
gcaccagatg ggacctactt ggccgctgtc cgccgcgctg cgttgactgg ccgcaccatg      5580
ctgtttaccc cgtcccagct tgggtctctt cttgagggtg ctttcagaac tcgaaagccc      5640
tcactgaaca ccgtcaatgt gatcgggtcc tccatgggct ctggcggggt gtttaccatc      5700
gacgggaaag tcaagtgcgt aactgccgca catgtcctta cgggcaattc agctcgggtt      5760
tccggggtcg gcttcaatca aatgcttgac tttgacgtaa agggagattt cgctatagct      5820
gattgcccga attggcaagg gctgccccc aagacccaat tctgcacgga tggatggact      5880
ggccgtgcct attggctaac atcctctggc gtcgaacccg cgtcattgg aaaaggattc      5940
gccttctgct tcaccgcatg tggcgattcc gggtccccag tgatcaccga ggccggtgag      6000
cttgtcggcg ttcacacggg atcgaataaa caagggggg gcattgttac gcgcccctca      6060
ggccagtttt gtaatgtggc acccatcaag ctaagcgaat taagtgaatt ctttgctggg      6120
cctaaggtcc cgctcggtga tgtgaaggtc ggcagccaca taattaaaga cataagcgag      6180
gtgccttcag atctttgtgc cttgcttgct gccaaacctg aactgaagg aggcctctcc      6240
accgtccaac ttctttgtgt gttttttctc ctgtggagaa tgatgggaca tgcctggacg      6300
```

-continued

```
cccttggttg ctgtgagttt ctttattttg aatgaggttc tcccagccgt cctggtccgg    6360
agtgttttct cctttggaat gtttgtgcta tcctggctca cgccatggtc tgcgcaagtt    6420
ctgatgatca ggcttctgac agcagctctt aacaggaaca gatggtcact tgccttttc    6480 agcctcggtg cagtgaccgg ttttgtcgca gatcttgcgg ccactcaggg catccgttg    6540 caggcagtga tgaatttgag cacctatgca ttcctgcctc ggatgatggt tgtgacctca    6600
ccagtcccag tgatcacgtg tggtgtcgtg cacctacttg ccatcatttt gtacttgttt    6660
aagtaccgtg gcccgcacca tatccttgtt ggcgatggag tgttctctgc ggctttcttc    6720
ttgagatact ttgccgaggg aaagttgagg aaggggtgt cgcaatcctg cggaatgaat     6780
catgagtctc tgactggtgc cctcgctatg agactcaatg acgaggactt ggatttcctt    6840
atgaaatgga ctgattttaa gtgctttgtt tctgcgtcca acatgaggaa tgcagcgggt    6900
caatttatcg aggctgccta tgctaaagca cttagagtag aactggccca gttggtgcag    6960
gttgataaag ttcgaggtac tttggccaaa cttgaagctt ttgctgatac cgtggcacct    7020
caactctcgc ccggtgacat tgttgtcgct ctcgccaca cgcctgttgg cagtatcttc     7080
gacctaaagg ttggtagcac caagcatacc ctccaagcca ttgagaccag agtccttgct    7140
gggtccaaaa tgaccgtggc gcgcgtcgtc gacccgaccc ccacgccccc acccgcaccc    7200
gtgcccatcc ccctcccacc gaaagttctg gagaatggcc caacgcttg ggggatgag     7260 gaccgtttga ataagaagaa gaggcgcagg atggaagccc tcggcatcta tgttatgggc    7320
gggaaaaagt accagaaatt tgggacaag aattccggtg atgtgttta tgaggaggtc     7380 cataataaca cagatgagtg ggagtgtctc agagttggcg accctgccga ctttgaccct    7440
gagaagggaa ctctgtgtgg acatgtcacc attgaaaaca aggcttacca tgtttacacc    7500
tccccatctg gtaagaagtt cttggtcccc gtcaacccag agaatggaag agttcaatgg    7560
gaagctgcaa agcttttccgt ggagcaggcc ctaggtatga tgaatgtcga cggcgaactg    7620
actgccaaag aactggagaa actgaaaaga ataattgaca aactccaggg cctgactaag    7680
gagcagtgtt taaactgcta gccgccagcg acttgacccg ctgtggtcgc ggcggcttgg    7740
ttgttactga aacagcggta aaatagtca aatttcacaa ccggaccttc accctgggac    7800
ctgtgaattt aaaagtggcc agtgaggttg agctaaaaga cgcggttgag cacaaccaac    7860
acccggttgc gagaccgatc gatggtggag ttgtgctcct gcgttccgcg gttccttcgc    7920
ttatagacgt cttgatctcc ggtgctgatg catctcccaa gttacttgcc catcacgggc    7980
cgggaaacac tgggatcgat ggcacgctct gggattttga gtccgaagcc actaaagagg    8040
aagtcgcact cagtgcgcaa ataatacagg cttgtgacat taggcgcggc gacgctcctg    8100
aaattggtct cccttacaag ctgtaccctg ttaggggtaa ccctgagcgg gtgaaaggag    8160
ttctgcagaa tacaaggttt ggagacatac cttacaaaac ccccagtgac actggaagcc    8220
cagtgcacgc ggctgcctgc cttacgccca acgccactcc ggtgactgat gggcgctccg    8280
tcttggccac gaccatgccc cccgggtttg agttatatgt accgaccata ccagcgtctg    8340
tccttgatta ccttgactct aggcctgact gccctaaaca gctgacagag cacggctgcg    8400
aagatgccgc actgaaagac ctctctaaat atgacttgtc cacccaaggc tttgttttac    8460
ctggagttct tcgccttgtg cggaaatacc tgtttgccca tgtaggtaag tgcccacccg    8520
ttcatcggcc ttctacttac cctgctaaga attctatggc tggaataaat gggaacaggt    8580
tcccaaccaa ggacattcag agcgtccctg aaatcgacgt tctgtgcgca caggctgtgc    8640
gagaaaactg gcaaactgtc accccttgta ctcttaagaa acagtattgc gggaagaaga    8700
```

```
agactaggac catactcggc accaataact tcatcgcact agcccaccga gcagtgttga    8760
gtggtgttac ccagggcttc atgaaaaagg cgtttaactc gcccatcgcc ctcggaaaga    8820
acaagtttaa ggagctacag actccggtcc tgggcaggtg ccttgaagct gatctcgcat    8880
cctgcgatcg atccacgcct gcaattgtcc gctggtttgc cgccaacctt ctttatgaac    8940
ttgcctgtgc tgaagagcat ctaccgtcgt acgtgctgaa ctgctgccac gacttactgg    9000
tcacgcagtc cggcgcagtg actaagagag gtggcctgtc gtctggcgac ccgatcacct    9060
ctgtgtctaa caccatttat agtttggtga tctatgcaca gcatatggtg cttagttact    9120
tcaaaagtgg tcaccccat ggccttctgt tcttacaaga ccagctaaag tttgaggaca     9180
tgctcaaggt tcaaccctg atcgtctatt cggacgacct cgtgctgtat gccgagtctc     9240
ccaccatgcc aaactatcac tggtgggttg aacatctgaa tttgatgctg ggtttcaga    9300
cggacccaaa gaagacagca ataacagact cgccatcatt tctaggctgt agaataataa    9360
atgggcgcca gctagtcccc aaccgtgaca ggatcctcgc ggccctcgcc tatcacatga    9420
aggcgagtaa tgtttctgaa tactatgcct cagcggctgc aatactcatg acagctgtg    9480
cttgttttgga gtatgatcct gaatggtttg aagaacttgt agttggaata gcgcagtgcg    9540
cccgcaagga cggctacagc tttcccggca cgccgttctt catgtccatg tgggaaaaac    9600
tcaggtccaa ttatgagggg aagaagtcga gagtgtgcgg gtactgcggg gccccggccc    9660
cgtacgctac tgcctgtggc ctcgacgtct gcatttacca cacccacttc caccagcatt    9720
gtccagtcac aatctggtgt ggccatccag cgggttctgg ttcttgtagt gagtgcaaat    9780
cccctgtagg gaaaggcaca agcccttag acgaggtgct ggaacaagtc ccgtataagc    9840
ccccacggac cgttatcatg catgtggagc agggtctcac cccccttgat ccaggtagat    9900
accaaactcg ccgcggatta gtctctgtca ggcgtggaat taggggaaat gaagttggac    9960
taccagacgg tgattatgct agcaccgcct tgctccctac ctgcaaagag atcaacatgg   10020
tcgctgtcgc ttccaatgta ttgcgcagca ggttcatcat cggcccaccc ggtgctggga   10080
aaacatactg gctccttcaa caggtccagg atggtgatgt tatttacaca ccaactcacc   10140
agaccatgct tgacatgatt agggctttgg ggacgtgccg gttcaacgtc ccggcaggca   10200
caacgctgca attccccgtc ccctcccgca ccggtccgtg ggttcgcatc ctagccggcg   10260
gttggtgtcc tggcaagaat tccttcctag atgaagcagc gtattgcaat caccttgatg   10320
ttttgaggct tcttagtaaa actaccctca cctgtctagg agacttcaag caactccacc   10380
cagtgggttt tgattctcat tgctatgttt ttgacatcat gcctcaaact caactgaaga   10440
ccatctggag gttggacag aatatctgtg atgccattca gccagattac agggacaaac    10500
tcatgtccat ggtcaacaca acccgtgtga cctacgtgga aaaacctgtc aggtatgggc   10560
aggtcctcac cccctaccac agggaccgag aggacgacgc catcactatt gactccagtc   10620
aaggcgccac attcgatgtg gttacattgc atttgcccac taaagattca ctcaacaggc   10680
aaagagccct tgttgctatc accagggcaa gacacgctat ctttgtgtat gacccacaca   10740
ggcagctgca gggcttgttt gatcttcctg caaaaggcac gcccgtcaac ctcgcagtgc   10800
actgcgacgg gcagctgatc gtgctggata gaaataacaa agaatgcacg gttgctcagg   10860
ctctaggcaa cggggataaa tttagggcca cagacaagcg tgttgtagat tctctccgcg   10920
ccatttgtgc tgatctagaa gggtcgagct ctccgctccc caaggtcgca cacaacttgg   10980
gattttattt ctcacctgat ttaacacagt ttgctaaact cccagtagaa cttgcacctc   11040
```

```
actggcccgt ggtgtcaacc cagaacaatg aaaagtggcc ggatcggctg gttgccagcc    11100
ttcgccctat ccataaatac agccgcgcgt gcatcggtgc cggctatatg gtgggccctt    11160
cggtgtttct aggcactcct ggggtcgtgt catactatct cacaaaattt gttaagggcg    11220
gggctcaagt gcttccggag acggttttca gcaccggccg aattgaggta gactgccggg    11280
aatatcttga tgatcgggag cgagaagttg ctgcgtccct cccacacggt ttcattggcg    11340
acgtcaaagg cactaccgtt ggaggatgtc atcatgtcac ctccagatac ctcccgcgcg    11400
tccttcccaa ggaatcagtt gcggtagtcg gggtttcaag ccccggaaaa gccgcgaaag    11460
cattgtgcac actgacagat gtgtacctcc cagatcttga agcctatctc cacccggaga    11520
cccagtccaa gtgctggaaa atgatgttgg acttcaaaga agttcgacta atggtctgga    11580
aagacaaaac agcctatttc caacttgaag gtcgctattt cacctggtat cagcttgcca    11640
gctatgcctc gtacatccgt gttcccgtca actctacggt gtacttggac ccctgcatgg    11700
gccccgccct ttgcaacagg agagtcgtcg gtccaccca ctgggggggct gacctcgcgg    11760
tcacccctta tgattacggc gctaaaatta tcctgtctag cgcgtaccat ggtgaaatgc    11820
cccccggata caaaattctg gcgtgcgcgg agttctcgtt ggatgaccca gttaagtaca    11880
aacatacctg ggggtttgaa tcggatacag cgtatctgta tgagttcacc ggaaacggtg    11940
aggactggga ggattacaat gatgcgtttc gtgcgcgcca ggaagggaaa atttataagg    12000
ccactgccac cagcttgaag ttttattttc ccccgggccc tgtcattgaa ccaactttag    12060
gcctgaattg aaatgaaatg gggtccatgc aaagcctttt tgacaaaatt ggccaacttt    12120
ttgtggatgc tttcacggag ttcttggtgt ccattgttga tatcattata ttttttggcca    12180
ttttgtttgg cttcaccatc gccggttggc tggtggtctt ttgcatcaga ttggtttgct    12240
ccgcgatact ccgtacgcgc cctgccattc actctgagca attacagaag atcttatgag    12300
gcctttcttt cccagtgcca agtggacatt cccacctggg gaactaaaca tccttttggg    12360
atgctttggc accataaggt gtcaaccctg attgatgaaa tggtgtcgcg tcgaatgtac    12420
cgcatcatgg aaaagcagg gcaggctgcc tggaaacagg tggtgagcga ggctacgctg    12480
tctcgcatta gtagtttgga tgtggtggct catttttcagc atctagccgc cattgaagcc    12540
gagacctgta atatttggc ctcccggctg cccatgctac acaacctgcg catgacaggg    12600
tcaaatgtaa ccatagtgta taatagcact ttgaatcagg tgtttgctat ttttccaacc    12660
cctggttccc ggccaaagct tcatgatttt cagcaatggt taatagctgt acattcctcc    12720
atattttcct ctgttgcagc ttcttgtact cttttttgttg tgctgtggtt gcgggttcca    12780
atactacgta ctgttttttgg tttccgctgg ttaggggcaa ttttttcttttc gaactcacag    12840
tgaattacac ggtgtgtcca ccttgcctca cccggcaagc agccacagag atctacgaac    12900
ccggtaggtc tctttggtgc aggataggggt atgaccgatg tggggaggac gatcatgacg    12960
agctagggtt tatgataccg cctggcctct ccagcgaagg ccacttgact ggtgtttacg    13020
cctggttggc gttcttgtcc ttcagctaca cggcccagtt ccatcccgag atattcggga    13080
tagggaatgt gagtcgagtt tatgttgaca tcaaacatca actcatctgc gccgaacatg    13140
acgggcagaa caccaccttg cctcgtcatg acaacatttc agccgtgttt cagacctatt    13200
accaacatca agtcgacggc ggcaattggt ttcacctaga atggcttcgt cccttctttt    13260
cctcgtggtt ggttttaaat gtctcttggt ttctcaggcg ttcgcctgca aaccatgttt    13320
cagttcgagt cttgcagata ttaagaccaa caccaccgca gcggcaagct tgctgtcct    13380
ccaagacatc agttgcctta ggcatcgcga ctcggcctct gaggcgattc gcaaaatccc    13440
```

```
tcagtgccgt acggcgatag ggacacccgt gtatgttacc atcacagcca atgtgacaga    13500
tgagaattat ttacattctt ctgatctcct catgctttct tcttgccttt tctatgcttc    13560
tgagatgagt gaaaagggat ttaaggtggt atttggcaat gtgtcaggca tcgtggctgt    13620
gtgtgtcaat tttaccagct acgtccaaca tgtcaaggag tttacccaac gctccctggt    13680
ggtcgaccat gtgcggttgc tccatttcat gacacctgag accatgaggt gggcaactgt    13740
tttagcctgt cttttttgcca ttctgttggc aatttgaatg tttaagtatg ttggagaaat    13800
gcttgaccgc gggctgttgc tcgcgattgc tttctttgtg gtgtatcgtg ccgttctgtt    13860
ttgctgtgct cgccaacgcc agcaacgaca gcagctccca tctacagctg atttacaact    13920
tgacgctatg tgagctgaat ggcacagatt ggctagctaa caaatttgat tgggcagtgg    13980
agagttttgt catctttccc gttttgactc acattgtctc ctatggtgcc ctcactacca    14040
gccatttcct tgacacagtc gctttagtca ctgtgtctac cgccgggttt gttcacgggc    14100
ggtatgtcct aagtagcatc tacgcggtct gtgccctggc tgcgttgact tgcttcgtca    14160
ttaggtttgc aaagaattgc atgtcctggc gctacgcgtg taccagatat accaactttc    14220
ttctggacac taagggcaga ctctatcgtt ggcggtcgcc tgtcatcata gagaaaaggg    14280
gcaaagttga ggtcgaaggt catctgatcg acctcaaaag agttgtgctt gatggttccg    14340
tggcaacccc tataaccaga gtttcagcgg aacaatgggg tcgtccttag atgacttctg    14400
tcatgatagc acggctccac aaaaggtgct tttggcgttt tctattacct acacgccagt    14460
gatgatatat gccctaaagg tgagtcgcgg ccgactgcta gggcttctgc accttttgat    14520
cttcctgaat tgtgctttca ccttcgggta catgactttc gcgcactttc agagtacaaa    14580
taaggtcgcg ctcactatgg gagcagtagt tgcactcctt tgggggtgt actcagccat    14640 agaaacctgg aaattcatca cctccagatg ccgtttgtgc ttgctaggcc gcaagtacat    14700
tctggcccct gcccaccacg ttgaaagtgc cgcacggttt catccgattg cggcaaatga    14760
taaccacgca tttgtcgtcc ggcgtcccgg ctccactacg gtcaacggca cattggtgcc    14820
cgggttaaaa agcctcgtgt tgggtggcag aaaagctgtt aaacagggag tggtaaacct    14880
tgtcaaatat gccaaataac aacggcaagc agcagaagag aaagaagggg gatggccagc    14940
cagtcaatca gctgtgccag atgctgggta agatcatcgc tcagcaaaac cagtccagag    15000
gcaagggacc gggaaagaaa aataagaaga aaaacccgga gaagccccat tttcctctag    15060
cgactgaaga tgatgtcaga catcacttta cccctagtga gcggcaattg tgtctgtcgt    15120
caatccagac cgcctttaat caaggcgctg ggacttgcac cctgtcagat tcagggagga    15180
taagttacac tgtggagttt agtttgccta cgcatcatac tgtgcgcctg atccgcgtca    15240
cagcatcacc ctcagcatga tgggctggca ttcttgaggc atctcagtgt ttgaattgga    15300
agaatgtgtg gtgaatggca ctgattgaca ttgtgcctct aagtcaccta ttcaattagg    15360
gcgaccgtgt gggggtgaga tttaattggc gagaaccatg cggccgaaat t             15411

<210> SEQ ID NO 2
<211> LENGTH: 939
<212> TYPE: DNA
<213> ORGANISM: Porcine reproductive and respiratory syndrome virus

<400> SEQUENCE: 2
atgtctggga tacttgatcg gtgcacgtgt acccccaatg ccagggtgtt tatggcggag      60
ggccaagtct actgcacacg atgcctcagt gcacggtctc tccttcccct gaacctccaa     120
```

-continued

```
gtttctgagc tcggggtgct aggcctattc tacaggcccg aagagccact ccggtggacg      180
ttgccacgtg cattcccac  tgttgagtgc tcccccgccg gggcctgctg gctttctgca      240
atctttccaa tcgcacgaat gaccagtgga aacctgaact tccaacaaag aatggtacgg      300
gtcgcagctg agctttacag agccggccag ctcacccctg cagtcttgaa ggctctacaa      360
gtttatgaac ggggttgccg ctggtacccc attgttggac ctgtccctgg agtggccgtt      420
ttcgccaatt ccctacatgt gagtgataaa cctttcccgg agcaactca  cgtgttgacc      480 aacctgccgc tcccgcagag acccaagcct gaagactttt gcccctttga gtgtgctatg      540
gctactgtct atgacattgg tcatgacgcc gtcatgtatg tggccgaaag gaaagtctcc      600
tgggcccctc gtggcgggga tgaagtgaaa tttgaagctg tccccgggga gttgaagttg      660
attgcgaacc ggctccgcac ctccttcccg ccccaccaca cagtggacat gtctaagttc      720
gccttcacag cccctgggtg tggtgtttct atgcgggtcg aacgccaaca cggctgcctt      780
cccgctgaca ctgtccctga aggcaactgc tggtggagct gtttgactt  gcttccactg      840 gaagttcaga acaaagaaat tcgccatgct aaccaatttg ctaccagac  caagcatggt      900 gtctctggca agtacctaca gcggaggctg caagttaat                             939
```

<210> SEQ ID NO 3
<211> LENGTH: 957
<212> TYPE: DNA
<213> ORGANISM: Porcine reproductive and respiratory syndrome virus

<400> SEQUENCE: 3

```
aatggtctcc gagcagtaac tgacctaaac ggacctatcg tcgtacagta cttctccgtt       60
aaggagagtt ggatccgcca tttgaaactg gcgggagaac ccagctactc tgggtttgag      120
gacctcctca gaataagggt tgagcctaac acgtcgccat tggctgacaa ggaagaaaaa      180
attttccggt ttggcagtca caagtggtac ggcgctggaa agagagcaag aaaagcacgc      240
tcttgtgcga ctgctacagt cgctggccgc gctttgtccg ttcgtgaaac ccggcaggcc      300
aaggagcacg aggttgccgg cgccaacaag gctgagcacc tcaaacacta ctcccccgcct      360 gccgaaggga attgtggttg gcactgcatt tccgccatcg ccaaccggat ggtgaattcc      420
aaatttgaaa ccacccttcc cgaaagagtg agacctccag atgactgggc tactgacgag      480
gatcttgtga atgccatcca atcctcaga  ctccctgcgg ccttagacag gaacggtgct      540
tgtactagcg ccaagtacgt acttaagctg gaaggtgagc attggactgt cactgtgacc      600
cctgggatgt cccttctttt gctccctctt gaatgtgttc agggctgttg tgggcacaag      660
ggcggtcttg gttccccaga tgcagtcgag gtctccggat ttgaccctgc ctgccttgac      720
cggctggctg aggtgatgca cctgcctagc agtgctatcc cagccgctct ggccgaaatg      780
tctggcgatt ccgatcgttc ggcttctccg gtcaccaccg tgtggactgt ttcgcagttc      840
tttgcccgtc acagcggagg gaatcaccct gaccaagtgc gcttagggaa attatcagc      900 ctttgtcagg tgattgagga ctgctgctgt tcccagaaca aaaccaaccg ggtcacc        957
```

<210> SEQ ID NO 4
<211> LENGTH: 976
<212> TYPE: DNA
<213> ORGANISM: Porcine reproductive and respiratory syndrome virus

<400> SEQUENCE: 4

```
cccggaggag gtcgcagcaa agattgacct gtacctccgt ggtgcaacaa atcttgaaga       60
atgcttggcc aggcttgaga aagcgcgccc gccacgcgta atcgacacct cctttgattg      120
```

```
ggatgttgtg ctccctgggg ttgaggcggc aacccagacg atcaagctgc cccaggtcaa    180
ccagtgtcgt gctctggtcc ctgttgtgac tcaaaagtcc ttggacaaca actcggtccc    240
cctgaccgcc ttttcactgg ctaactacta ctaccgtgcg caaggtgacg aagttcgtca    300
ccgtgaaaga ctaaccgccg tgctctccaa gttggaaaag gttgttcgag aagaatatgg    360
gctcatgcca accgagcctg gtccacggcc acactgccca cgcgggctcg acgaactcaa    420
agaccagatg gaggaggact tgctgaaact ggctaacgcc cagacgactt cggacatgat    480
ggcctgggca gtcgagcagg ttgacctaaa aacttgggtc aagaactacc gcgcgtggac    540
accaccaccc cctccgccaa aagttcagcc tcgaaaaacg aagcctgtca gagcttgcc    600
ggagagaaag cctgtccccg ccccgcgcag gaaggttggg tccgattgtg cagcccggt    660
ttcattaggc ggcgatgtcc ctaacagttg gaagatttg gctgttagta gccccttga    720
tctcccgacc ccacctgagc cggcaacacc ttcaagtgag ctggtgattg tgtcctcacc    780
gcaatgcatc ttcaggccgg cgacacccttt gagtgagccg gctccaattc ccgcacctcg    840
cggaactgtg tctcgaccgg tgacacccttt gagtgagccg atccctgtgc ccgcaccgcg    900
gcgtaagttt cagcaggtga aaagattgag ttcggcggcg gcaatcccac cgtaccagga    960
cgagcccctg gatttg                                                     976

<210> SEQ ID NO 5
<211> LENGTH: 954
<212> TYPE: DNA
<213> ORGANISM: Porcine reproductive and respiratory syndrome virus

<400> SEQUENCE: 5
caggacgagc ccctggattt gtctgcttcc tcacagactg aatatgaggc ctctccccca     60
gcaccgccgc agagcggggg cgttctggga gtagaggggc atgaagctga ggaaaccctg    120
agtgaaatct cggacatgtc gggtaacatt aaacctgcgt ccgtgtcatc aagcagctcc    180
ttgtccagcg tgagaatcac acgcccaaaa tactcagctc aagccatcat cgactcgggc    240
gggcccctgca gtgggcatct ccaagaggta aggaaacat gccttagtgt catgcgcgag    300
gcatgtgatg cgactaagct tgatgaccct gctacgcagg aatggcttc tcgcatgtgg    360
gatcgggtgg acatgctgac ttggcgcaac acgtctgttt accaggcgat ttgcaccttta    420
gatggcaggt taaagttcct cccaaaaatg atactcgaga caccgccgcc ctatccgtgt    480
gagtttgtga tgatgcctca cacgcctgca ccttccgtag gtgcggagag cgaccttacc    540
attggctcag ttgctactga agatgttcca cgcatcctcg agaaaataga aatgtcggc    600
gagatggcca accagggacc cttggccttc tccgaggata aaccggtaga tgaccaactt    660
gtcaacgacc cccggatatc gtcgcggagg cctgacgaga gcacatcagc tccgtccgca    720
ggcacaggtg gcgccggctc tttttaccga ttgccgccttt cagatggcgc ggatgcggac    780
ggggggggc cgtttcggac ggtaaaaaga aaagctgaaa ggctctttga ccaactgagc    840
cgtcaggttt ttgacctcgt ctcccatctc cctgttttct tctcacgcct tttctaccct    900
ggcggtggtt attctccggg tgattggggt tttgcagctt ttactctatt gtgc         954

<210> SEQ ID NO 6
<211> LENGTH: 939
<212> TYPE: DNA
<213> ORGANISM: Porcine reproductive and respiratory syndrome virus

<400> SEQUENCE: 6
```

-continued

| | |
|---|---|
| ttgtgcctct ttttatgtta cagttaccca gcctttggta ttgctcccct cttgggtgtg | 60 |
| ttttctgggt cttctcggcg cgttcgaatg ggggttttg gctgctggtt ggcttttgct | 120 |
| gttggtctgt tcaagcctgt gtccgaccca gtcggcgctg cttgtgagtt tgactcgcca | 180 |
| gagtgtagaa acatccttca ttcttttgag cttctcaaac cttgggaccc tgttcgcagc | 240 |
| cttgttgtgg gccccgtcgg tctcggtctt gccattcttg gcaggttact gggcggggca | 300 |
| cgctgcatct ggcactttt gcttaggctt ggcattgttg cagactgtat cttggctgga | 360 |
| gcttacgtgc tttctcaagg taggtgtaaa aagtgctggg gatcttgtat aagaactgct | 420 |
| cctaatgagg tcgcttttaa cgtgtttcct ttcacacgtg cgaccaggtc gtcacttatc | 480 |
| gacctgtgcg atcggttttg tgcgccaaaa ggaatggacc ccatttttct cgccactggg | 540 |
| tggcgcgggt gctgggccgg ccgaagcccc attgagcaac cctctgaaaa acccatcgcg | 600 |
| tttgcccaat tggatgaaaa gaagattacg ctaggactg tggtcgccca gccttatgac | 660 |
| cccaaccaag ccgtaaagtg cttgcgggta ttgcagtcgg gtggggcgat ggtggctaag | 720 |
| gcggtcccaa aagtggtcaa ggtttccgct gttccattcc gagcccccctt ctttcccact | 780 |
| ggagtgaaag ttgaccctga ttgcagggtc gtggttgacc ctgacacttt cactgcagct | 840 |
| ctccggtctg gctactccac cacaaaacctc gtccttggtg taggggactt tgcccagctg | 900 |
| aatggattaa aaatcaggca aatttccaag ccttcaggg | 939 |

<210> SEQ ID NO 7
<211> LENGTH: 957
<212> TYPE: DNA
<213> ORGANISM: Porcine reproductive and respiratory syndrome virus

<400> SEQUENCE: 7

| | |
|---|---|
| ggaggcccac atctcatggc tgccctgcat gttgcctgct cgatggctct gcacatgctt | 60 |
| gctgggattt atgtgactgc ggtgggttct tgcggcaccg gcaccaacga cccgtggtgc | 120 |
| gctaacccgt ttgccgtccc tggctacgga cctggctctc tctgcacgtc caggttgtgc | 180 |
| atttcccaac acggccttac cctgcccttg acagcacttg tggcgggatt cggtattcaa | 240 |
| gaaattgcct tggtcgtttt gattttgtt tccatcggag gcatggctca taggttgagc | 300 |
| tgtaaggctg acatgctgtg tgttttgctt gcaattgcca gctatgtttg ggtacctctt | 360 |
| acctggttgc tttgtgtgtt tccttgctgg ttgcgctgtt tttctttgca cccctcacc | 420 |
| atcctatggt tggtgttttt cttgatttct gtgaatatgc cttcaggaat cttggccatg | 480 |
| gtgttgttgg tttctctttg gcttcttggt cgttatacta atgttgctgg ccttgtcacc | 540 |
| ccctacgaca tcatcatta caccagtggc cccgcggtg ttgccgcctt ggctaccgca | 600 |
| ccagatggga cctacttggc cgctgtccgc cgcgctgcgt tgactggccg caccatgctg | 660 |
| tttaccccgt cccagcttgg gtctcttctt gagggtgctt tcagaactcg aaagccctca | 720 |
| ctgaacaccg tcaatgtgat cgggtcctcc atgggctctg gcggggtgtt taccatcgac | 780 |
| gggaaagtca agtgcgtaac tgccgcacat gtccttacgg gcaattcagc tcgggtttcc | 840 |
| ggggtcggct tcaatcaaat gcttgacttt gacgtaaagg gagatttcgc tatagctgat | 900 |
| tgcccgaatt ggcaagggc tgccccaag acccaattct gcacggatgg atggact | 957 |

<210> SEQ ID NO 8
<211> LENGTH: 957
<212> TYPE: DNA
<213> ORGANISM: Porcine reproductive and respiratory syndrome virus

<400> SEQUENCE: 8

-continued

```
tgcacggatg gatggactgg ccgtgcctat tggctaacat cctctggcgt cgaacccggc      60
gtcattggaa aaggattcgc cttctgcttc accgcatgtg gcgattccgg gtccccagtg     120
atcaccgagg ccggtgagct tgtcggcgtt cacacgggat cgaataaaca aggggggggc     180
attgttacgc gcccctcagg ccagttttgt aatgtggcac ccatcaagct aagcgaatta     240
agtgaattct tgctgggcc taaggtcccg ctcggtgatg tgaaggtcgg cagccacata     300
attaaagaca taagcgaggt gccttcagat cttttgtgcct tgcttgctgc caaacctgaa    360
ctggaaggag gcctctccac cgtccaactt cttttgtgtgt ttttctcct gtggagaatg     420
atgggacatg cctggacgcc cttggttgct gtgagtttct ttattttgaa tgaggttctc     480
ccagccgtcc tggtccggag tgttttctcc tttggaatgt ttgtgctatc ctggctcacg     540
ccatggtctg cgcaagttct gatgatcagg cttctgacag cagctcttaa caggaacaga    600
tggtcacttg ccttttttcag cctcggtgca gtgaccggtt ttgtcgcaga tcttgcggcc    660
actcagggc atccgttgca ggcagtgatg aatttgagca cctatgcatt cctgcctcgg    720
atgatggttg tgacctcacc agtcccagtg atcacgtgtg tgtcgtgca cctacttgcc    780
atcatttgt acttgtttaa gtaccgtggc ccgcaccata tccttgttgg cgatggagtg    840
ttctctgcgg cttcttctt gagatacttt gccgagggaa agttgaggga aggggtgtcg    900
caatcctgcg gaatgaatca tgagtctctg actggtgccc tcgctatgag actcaat      957
```

<210> SEQ ID NO 9
<211> LENGTH: 852
<212> TYPE: DNA
<213> ORGANISM: Porcine reproductive and respiratory syndrome virus

<400> SEQUENCE: 9

```
atgagactca atgacgagga cttggatttc cttatgaaat ggactgattt taagtgcttt     60
gtttctgcgt ccaacatgag gaatgcagcg ggtcaattta tcgaggctgc ctatgctaaa    120
gcacttagag tagaactggc ccagttggtg caggttgata agttcgagg tactttggcc   180
aaacttgaag cttttgctga taccgtggca cctcaactct cgcccggtga cattgttgtc    240
gctctcggcc acacgcctgt tggcagtatc ttcgacctaa aggttggtag caccaagcat    300
accctccaag ccattgagac cagagtcctt gctgggtcca aaatgaccgt ggcgcgcgtc    360
gtcgacccga ccccacgcc cccacccgca cccgtgccca tccccctccc accgaaagtt    420
ctggagaatg cccccaacgc ttgggggggat gaggaccgtt tgaataagaa gaagaggcgc    480
aggatggaag ccctcggcat ctatgttatg ggcgggaaaa agtaccagaa attttgggac   540
aagaattccg gtgatgtgtt ttatgaggag gtccataata cacagatga gtgggagtgt     600
ctcagagttg gcgaccctgc cgactttgac cctgagaagg gaactctgtg tggacatgtc    660
accattgaaa acaaggctta ccatgtttac acctccccat ctggtaagaa gttcttggtc    720
cccgtcaacc cagagaatgg aagagttcaa tgggaagctg caaagctttc cgtggagcag    780
gcccctaggta tgatgaatgt cgacggcgaa ctgactgcca agaactgga gaaactgaaa    840
agaataattg ac                                                       852
```

<210> SEQ ID NO 10
<211> LENGTH: 917
<212> TYPE: DNA
<213> ORGANISM: Porcine reproductive and respiratory syndrome virus

<400> SEQUENCE: 10

-continued

| | |
|---|---|
| gcttggttgt tactgaaaca gcggtaaaaa tagtcaaatt tcacaaccgg accttcaccc | 60 |
| tgggacctgt gaatttaaaa gtggccagtg aggttgagct aaaagacgcg gttgagcaca | 120 |
| accaacaccc ggttgcgaga ccgatcgatg gtggagttgt gctcctgcgt tccgcggttc | 180 |
| cttcgcttat agacgtcttg atctccggtg ctgatgcatc tcccaagtta cttgcccatc | 240 |
| acgggccggg aaacactggg atcgatggca cgctctggga ttttgagtcc gaagccacta | 300 |
| aagaggaagt cgcactcagt gcgcaaataa tacaggcttg tgacattagg cgcggcgacg | 360 |
| ctcctgaaat tggtctccct tacaagctgt accctgttag gggtaaccct gagcgggtga | 420 |
| aaggagttct gcagaataca aggtttggag acataccta caaaaccccc agtgacactg | 480 |
| gaagcccagt gcacgcggct gcctgcctta cgcccaacgc cactccggtg actgatgggc | 540 |
| gctccgtctt ggccacgacc atgccccccg ggtttgagtt atatgtaccg accataccag | 600 |
| cgtctgtcct tgattacctt gactctaggc ctgactgccc taaacagctg acagagcacg | 660 |
| gctgcgaaga tgccgcactg aaagacctct ctaaatatga cttgtccacc caaggctttg | 720 |
| ttttacctgg agttcttcgc cttgtgcgga aatacctgtt tgcccatgta ggtaagtgcc | 780 |
| cacccgttca tcggccttct acttaccctg ctaagaattc tatggctgga ataaatggga | 840 |
| acaggttccc aaccaaggac attcagagcg tccctgaaat cgacgttctg tgcgcacagg | 900 |
| ctgtgcgaga aaactgg | 917 |

<210> SEQ ID NO 11
<211> LENGTH: 972
<212> TYPE: DNA
<213> ORGANISM: Porcine reproductive and respiratory syndrome virus

<400> SEQUENCE: 11

| | |
|---|---|
| gctgtgcgag aaaactggca aactgtcacc ccttgtactc ttaagaaaca gtattgcggg | 60 |
| aagaagaaga ctaggaccat actcggcacc aataacttca tcgcactagc ccaccgagca | 120 |
| gtgttgagtg gtgttaccca gggcttcatg aaaaaggcgt ttaactcgcc catcgccctc | 180 |
| ggaaagaaca agtttaagga gctacagact ccggtcctgg gcaggtgcct tgaagctgat | 240 |
| ctcgcatcct gcgatcgatc cacgcctgca attgtccgct ggtttgccgc caaccttctt | 300 |
| tatgaacttg cctgtgctga agagcatcta ccgtcgtacg tgctgaactg ctgccacgac | 360 |
| ttactggtca cgcagtccgg cgcagtgact aagagaggtg gcctgtcgtc tggcgacccg | 420 |
| atcacctctg tgtctaacac catttatagt ttggtgatct atgcacagca tatggtgctt | 480 |
| agttacttca aaagtggtca cccccatggc cttctgttct tacaagacca gctaaagttt | 540 |
| gaggacatgc tcaaggttca accctgatc gtctattcgg acgacctcgt gctgtatgcc | 600 |
| gagtctccca ccatgccaaa ctatcactgg tgggttgaac atctgaattt gatgctgggg | 660 |
| tttcagacgg acccaaagaa acagcaata acagactcgc catcatttct aggctgtaga | 720 |
| ataataaatg ggcgccagct agtccccaac cgtgacagga tcctcgcggc cctcgcctat | 780 |
| cacatgaagg cgagtaatgt ttctgaatac tatgcctcag cggctgcaat actcatggac | 840 |
| agctgtgctt gtttggagta tgatcctgaa tggtttgaag aacttgtagt tggaatagcg | 900 |
| cagtgcgccc gcaaggacgg ctacagcttt cccggcacgc cgttcttcat gtccatgtgg | 960 |
| gaaaaactca gg | 972 |

<210> SEQ ID NO 12
<211> LENGTH: 966
<212> TYPE: DNA
<213> ORGANISM: Porcine reproductive and respiratory syndrome virus

<400> SEQUENCE: 12

```
atgtgggaaa aactcaggtc caattatgag gggaagaagt cgagagtgtg cgggtactgc    60
ggggccccgg ccccgtacgc tactgcctgt ggcctcgacg tctgcattta ccacacccac   120
ttccaccagc attgtccagt cacaatctgg tgtggccatc cagcgggttc tggttcttgt   180
agtgagtgca atcccctgt agggaaaggc acaagccctt tagacgaggt gctggaacaa   240
gtcccgtata agcccccacg gaccgttatc atgcatgtgg agcagggtct cacccccctt   300
gatccaggta gataccaaac tcgccgcgga ttagtctctg tcaggcgtgg aattagggga   360
aatgaagttg gactaccaga cggtgattat gctagcaccg ccttgctccc tacctgcaaa   420
gagatcaaca tggtcgctgt cgcttccaat gtattgcgca gcaggttcat catcggccca   480
cccggtgctg ggaaaacata ctggctcctt caacaggtcc aggatggtga tgttatttac   540
acaccaactc accagaccat gcttgacatg attagggctt tggggacgtg ccggttcaac   600
gtcccggcag gcacaacgct gcaattcccc gtccctcccc gcaccggtcc gtgggttcgc   660
atcctagccg gcggttggtg tcctggcaag aattccttcc tagatgaagc agcgtattgc   720
aatcaccttg atgttttgag gcttcttagt aaaactaccc tcacctgtct aggagacttc   780
aagcaactcc acccagtggg ttttgattct cattgctatg ttttgacat catgcctcaa   840
actcaactga agaccatctg gaggtttgga cagaatatct gtgatgccat tcagccagat   900
tacagggaca aactcatgtc catggtcaac acaacccgtg tgacctacgt ggaaaaacct   960
gtcagg                                                             966
```

<210> SEQ ID NO 13
<211> LENGTH: 783
<212> TYPE: DNA
<213> ORGANISM: Porcine reproductive and respiratory syndrome virus

<400> SEQUENCE: 13

```
gtggaaaaac ctgtcaggta tgggcaggtc ctcacccccct accacaggga ccgagaggac    60
gacgccatca ctattgactc cagtcaaggc gccacattcg atgtggttac attgcatttg   120
cccactaaag attcactcaa caggcaaaga gcccttgttg ctatcaccag gcaagacac   180
gctatctttg tgtatgaccc acacaggcag ctgcagggct gtttgatct tcctgcaaaa   240
ggcacgcccg tcaacctcgc agtgcactgc gacgggcagc tgatcgtgct ggatagaaat   300
aacaaagaat gcacggttgc tcaggctcta ggcaacgggg ataaatttag gccacagac   360
aagcgtgttg tagattctct ccgcgccatt tgtgctgatc tagaagggtc gagctctccg   420
ctcccccaagg tcgcacacaa cttgggattt tatttctcac ctgatttaac acagtttgct   480
aaactcccag tagaacttgc acctcactgg cccgtggtgt caacccagaa caatgaaaag   540
tggccggatc ggctggttgc cagccttcgc cctatccata atacagccg cgcgtgcatc   600
ggtgccggct atatggtggg ccccttcggtg tttctaggca ctcctggggt cgtgtcatac   660
tatctcacaa aatttgttaa gggcgggct caagtgcttc cggagacggt tttcagcacc   720
ggccgaattg aggtagactg cccgggaatat cttgatgatc gggagcgaga agttgctgcg   780
tcc                                                                783
```

<210> SEQ ID NO 14
<211> LENGTH: 774
<212> TYPE: DNA
<213> ORGANISM: Porcine reproductive and respiratory syndrome virus -continued

```
<400> SEQUENCE: 14
gagcgagaag ttgctgcgtc cctcccacac ggtttcattg gcgacgtcaa aggcactacc        60
gttggaggat gtcatcatgt cacctccaga tacctcccgc gcgtccttcc caaggaatca       120
gttgcggtag tcggggtttc aagccccgga aaagccgcga aagcattgtg cacactgaca       180
gatgtgtacc tcccagatct tgaagcctat ctccacccgg agacccagtc caagtgctgg       240
aaaatgatgt tggacttcaa agaagttcga ctaatggtct ggaaagacaa aacagcctat       300
ttccaacttg aaggtcgcta tttcacctgg tatcagcttg ccagctatgc ctcgtacatc       360
cgtgttcccg tcaactctac ggtgtacttg gaccctgca tgggcccgc cctttgcaac        420 aggagagtcg tcgggtccac ccactggggg gctgacctcg cggtcacccc ttatgattac       480
ggcgctaaaa ttatcctgtc tagcgcgtac catggtgaaa tgcccccgg atacaaaatt        540 ctggcgtgcg cggagttctc gttggatgac ccagttaagt acaaacatac ctgggggttt       600
gaatcggata cagcgtatct gtatgagttc accggaaacg gtgaggactg ggaggattac       660
aatgatgcgt ttcgtgcgcg ccaggaaggg aaaatttata aggccactgc caccagcttg       720
aagttttatt ttcccccggg ccctgtcatt gaaccaactt taggcctgaa ttga             774
```

PRRSV SUBUNIT VACCINES

RELATED APPLICATIONS

This application claims the benefit of Provisional Application Ser. No. 60/581,350, filed on Jun. 17, 2004, the teachings and content of which are expressly incorporated by reference herein.

SEQUENCE LISTING

A printed Sequence Listing accompanies this application, and has also been submitted with identical contents in the form of a computer readable ASCII file on a CD-ROM.

BACKGROUND OF THE INVENTION

1. Field of the Invention

The present invention is broadly concerned with vaccines for porcine reproductive and respiratory syndrome (PRRS). More particularly, the invention is concerned with the prevention of PRRS in swine by the administration of a vaccine comprising DNA subunits of PRRS virus (PRRSV). Still more particularly, the invention pertains to the use of open reading frame 1 (ORF1) in a DNA subunit vaccine which provides protective immunity against PRRSV to swine. Even more particularly, the invention pertains to the use of selected portions of ORF1 both alone and in combination with other portions of the PRRSV genome or in combination with other vaccines against PRRSV.

2. Description of the Prior Art

PRRS is a major disease in the swine industry worldwide. PRRS is caused by PRRSV infection. Currently, there are modified-live vaccines (MLV) available that, when used correctly, provide swine with protection against the clinical disease resulting from PRRSV infection. PRRS MLV vaccines require replication in the vaccinated animal in order to insure that an efficacious immune response is induced (for example, see Meng, X. J., Heterogeneity of Porcine Reproductive and Respiratory Syndrome Virus: Implications for Current Vaccine Efficacy and Future Vaccine Development; 74 Vet. Micro., 309-329 (2000)). However, such replication presents problems in that the PRRS MLV can persist in the animal for several weeks after vaccination and can also be shed to other PRRSV-negative swine. The shedding of PRRS MLV from vaccinated animals can be a problem in some swine herds that do not have good biosecurity measures in place to prevent shedding of PRRSV MLV from vaccinated animals to a PRRSV-naive population. Although millions of PRRS MLV doses have been used without issue, there are also sporadic reports in the literature as to the ability of the PRRS MLV to revert to a more virulent, wild-type strain of PRRSV. Attempts to solve the problems of PRRS MLV shed and possible reversion to virulence have also been tried by utilization of a vaccine comprised of inactivated PRRS virus (i.e. PRRS KV). However, research has shown that despite the fact that PRRS KV can induce a strong humoral response in vaccinated swine, it is not effective in preventing PRRS-associated disease.

Accordingly, what is needed in the art is a method of vaccination and vaccine that could induce the protective immune response, without the problems associated with PRRS MLV. Preferably, administration of the vaccine would not actively replicate in the vaccinated animal and would induce a strong humoral and cell-mediated immune response.

SUMMARY OF THE INVENTION

The present invention solves the problems inherent and the prior art provides a distinct advance in the state of the art by providing PRRSV DNA vaccines. Theoretically, the DNA vaccine plasmid expressing the PRRS antigen serves as a template to synthesize PRRSV antigens (i.e. like a PRRS MLV), but also has the characteristic of not actively replicating in the animal (i.e. like a PRRS KV). The protective immunogens needed to induce a protective host response to PRRSV are not known. Since the PRRS MLV can induce a protective response in vaccinated swine, it is thought that the replication of the PRRS MLV in the vaccinated animal must induce both a strong humoral and cell-mediated immune response in the vaccinated animal.

ORF1 of PRRSV encodes for the replication machinery necessary for PRRSV replication and generation of new progeny. ORF1 has two regions, designated as ORF1a and ORF1b, that comprise the ORF1 replicase complex (Dea, et al., Current Knowledge on the Structural Proteins of Porcine Reproductive and Respiratory Syndrome (Prrs) Virus: Comparison of the North American and European Isolates; 145 (4) Archives of Virology, 659-688 (2000)). The replicase-encoded proteins are thought to be key immunogens in other virus families (Leitner et al., DAN and RNA-Based Vaccines: Principles, Progress and Prospects; 18 Vaccine 765-777 (2000)). When a cell is infected with PRRSV, the activity of the viral replicase may provide a powerful adjuvant-effect as the replicase-associated antigens are expressed during infection of the cell. The replicase-associated antigens may serve as "danger signals" generated in transfected cells and induce strong host immune responses (i.e. WFN, HSP, apoptosis). Thus, replicase-associated "danger signals" could be a key factor in why PRRS MLV can induce protection whereas a non-replicating PRRS (i.e. inactivated antigen in PRRS KV) does not confer protection from challenge.

ORF1 is nearly 12,000 nucleotides in length which makes transfection and adequate expression in a eukaryotic cell difficult. Thus, ORF1 was sequentially and arbitrarily divided up into smaller sections using Expression Library Immunization (ELI) as a tool to determine the protective immunogens of various pathogens. ELI shears the genome of a particular pathogen into small fragments that are cloned into a DNA vaccine vector and thereafter administered to a host to determine if any fragment is capable of inducing an immune response (Johnston and Barry; Genetic to Genomic Vaccination; 15(8) Vaccine, 808-809 (1997)). Preferably, the immune response is protective. The invention is predicated on the hypothesis that host immune responses to ORF1-generated proteins are essential for protection from PRRSV challenge. It is relatively easy to place the regions encoding for PRRSV ORFs 2-7 in a DNA vaccine vector since these ORFs range from 317-720 nucleotides in length. As noted above, the size of the ORF1 region of PRRSV is nearly 12,000 nucleotides in length. Placing a region of this size into a DNA vaccine vector would not be amenable to transfection and subsequent expression in a eukaryotic cell. Accordingly, it was essential to break the ORF1 region into smaller sections to better ensure adequate expression of all areas of ORF1. Expression Library Immunization (ELI) has been employed as a tool to determine the protective immunogens of various pathogens. ELI employs that shearing of the genome of a particular pathogen into small fragments. These small fragments are then cloned into a DNA vaccine vector and then administered to the host to determine if any fragment is capable of inducing a protective immune response. Herein, the ELI technique has been modified for development of a PRRSV DNA vaccine that is sequentially comprised of the ORF 1 encoding region of the PRRSV genome. This method has been designated as SELI (sequential expression library immunization). This is in contrast to Barfoed et al., (DNA Vaccination of Pigs with Open Reading Frame 1-7 of PRRS Virus; 22 Vaccine, 3628-3641 (2004)) that used the entire ORF1 region as a DNA vaccine.

Vaccines of the present invention comprise portions of PRRSV ORF1 alone, in combination with other portions of PRRSV ORF1, and together with other compositions effective at generating an immune response to PRRSV infection including other PRRSV vaccines. ORF1 portions useful for purposes of the present invention are of sufficient size to invoke an immune response in an animal receiving the vaccine. Preferably, the portion will include up to about 9,000 base pairs, More preferably, the ORF-1 portion will include between about 21-9,000 contiguous nucleotide base pairs, still more preferably between about 21-6,000 contiguous nucleotide base pairs, even more preferably between about 21-3,000 contiguous nucleotide base pairs, still more preferably between about 21-2,000 contiguous nucleotide base pairs, even more preferably between about 21-1,000 contiguous nucleotide base pairs, still more preferably between about 21-500 contiguous nucleotide base pairs, even more preferably between about 21-300 contiguous nucleotide base pairs, still more preferably between about 21-150 contiguous nucleotide base pairs, even more preferably between about 21-75 contiguous nucleotide base pairs, still more preferably between about 21-50 contiguous nucleotide base pairs, even more preferably between about 21-25 contiguous nucleotide base pairs, still more preferably between about 21-23, and most preferably at least about 21 contiguous nucleotide base pairs. The protein resulting from any one of these preferred portions is also a part of the present invention. Any ORF1 or portion thereof from any strain of PRRSV could be used for purposes of the present invention, however, it is preferred to use a strain that is virulent.

The selected portion(s) can be cloned into a suitable expression vector. Examples of suitable vectors include adenovirus vectors, Shigella vectors, pVC1650 (Valentis, Inc., Burlingame, Calif.), WRG720 (W. R. Grace, New York, N.Y.) and pcDNA3 (Invitrogen, Carlsbad, Calif.). Some preferred vectors contain the immediate early cytomegalovirus promoter, intron A, and a poly-a adenylation portion (e.g. Bovine growth hormone (BGH) or human growth hormone (HGH)). Additionally, purified PRRSV proteins could be expressed in insect cell culture using, for example, the baculovirus expression system. Such proteins could then be combined with an adjuvant and administered. Of course, those of skill in the art would be able to select suitable expression systems and vectors that can direct the expression of various PRRSV ORFs in eukaryotic cells. Preferably, after cloning the respective portions of ORF1 into a suitable expression vector, the orientation of the clone is verified.

In one example of the present invention, the PRRSV virus VR-2332 was selected for use in accordance with the present invention. Genbank U87392 was used to generate 13 overlapping clones of ORF1. This ORF1 includes 12,071 nucleotide base pairs. The portions ranged in size from 773 bp to 975 bp. The clones were designated with the letters A-M with clone A (SEQ ID No. 2) being 939 bp, clone B (SEQ ID No. 3) being 957 bp, clone C (SEQ ID No. 4) being 976, clone D (SEQ ID No. 5) being 954 bp, clone E (SEQ ID No. 6) being 939 bp, clone F (SEQ ID No. 7) being 957 bp, clone G (SEQ ID No. 8) being 957 bp, clone H (SEQ ID No. 9) being 852 bp, clone I (SEQ ID No. 10) being 917 bp, clone J (SEQ ID No. 11) being 972 bp, clone K (SEQ ID No. 12) being 966 bp, clone L (SEQ ID No. 13) being 783 bp, and clone M (SEQ ID No. 14) being 774 bp. Clones A-H are from region 1a and clones I-M are from region 1b of ORF1. Clone A utilizes the authentic ORF1A ATG start codon. The remaining ORF1 clones had an inframe ATG start codon added to their five prime ends. Each of these clones were respectively cloned into the DNA expression vector pVC1650. This vector contains the immediate early cytomegalovirus promoter and intron A and directs the expression of the various PRRSV ORFs in eukaryotic cells. Table 1 provides information regarding each clone and which region of the nucleotide sequence each clone is derived from.

TABLE 1

BIV PRRSV ORF1a/1b Sequential Expression Library Immunization (SELI) Clones

| SEQ ID | ORF1 SELI Clone | Size (base pairs) | Region of clone | Nucleotide span of clone (using Genbank U87392 as reference) | Status Cloned into expression vector pVC1650 and orientation verified | IFA reaction following transfection using procine anti-PRRSV convalescent sera |
|---|---|---|---|---|---|---|
| 2 | A | 939 | ORF 1a | 190-1128 | ✓ | ⊕ |
| 3 | B | 957 | ORF 1a | 1126-2082 | ✓ | ⊕ |
| 4 | C | 976 | ORF 1a | 2082-3057 | ✓ | ⊕ |
| 5 | D | 954 | ORF 1a | 3037-3990 | ✓ | ⊕ |
| 6 | E | 939 | ORF 1a | 3985-4923 | ✓ | ⊕ |
| 7 | F | 957 | ORF 1a | 4924-5880 | ✓ | — |
| 8 | G | 957 | ORF 1a | 5863-6819 | ✓ | — |
| 9 | H* | 852 | ORF 1a | 6808-7659 | ✓ | ⊕ |
| 10 | I* | 917 | ORF 1b | 7735-8651 | ✓ | — |
| 11 | J | 972 | ORF 1b | 8634-9605 | ✓ | weak ⊕ |
| 12 | K | 966 | ORF 1b | 9588-10553 | ✓ | — |
| 13 | L | 783 | ORF 1b | 10536-11318 | ✓ | — |
| 14 | M | 774 | ORF 1b | 11298-12071 | ✓ | — |

*Note: Original H and I clones flank the ORF1a/1b minus 1 frameshift region and new primers were designed to give slightly smaller RT-PCR products.

Each portion was then utilized in various combinations as well as alone in vaccine preparations comprising other PRRSV ORFs.

In another example, clones A-M and clones of ORFs 2-6 were cloned into the pVC 1650 expression vector and a clone for ORF7 was cloned into the WRG720 expression vector. Of course, those of skill in the art will be able to select suitable vectors. Additionally, the nucleic acid sequences of the present invention can be produced by standard techniques, including, without limitation, common molecular cloning, mutagenesis, and chemical nucleic acid synthesis techniques. For purposes of the present invention, DNA sequences having at least 75% sequence identity, more preferably at least 75%, even more preferably at least 80%, still more preferably at least 85%, even more preferably at least 90%, still more preferably at least 95%, even more preferably at least 98%, more preferably at least 99% and most preferably 100% sequence identity with any one of clones A-M would be covered by the present invention.

In one aspect of the present invention, each of the clones A-M are used individually as a vaccine component. Animals are immunized with the vaccine by administration by any conventional means. Examples of administration methods include oral, transdermal, intravenous, subcutaneous, intramuscular, intraocular, intraperitoneal, intrarectal, intravaginal, intranasal, intragastrical, intratracheal, intrapulmonarial, or any combination thereof. Preferred modes of administration are intramuscular, subcutaneous and intranasal. If desired or necessary, booster immunizations may be given once or several times at various intervals. After administration of such a vaccine, an immune response is elicited in the animal and clinical signs of PRRSV infection are reduced in incidence and/or severity after challenge with a virulent form of PRRSV.

In another aspect of the present invention, combinations of clones A-M are administered to animals as described above. Such combinations include two or more of the above-referenced clones. Because some of these clones (A, B, C, D, E, H, and J) elicited an IFA reaction following transfection using porcine anti-PRRSV convalescent sera, combinations of these clones are preferred for purposes of the present invention.

In another aspect of the present invention, clones A-M, either individually or in combinations as described above, are used in combinations with other ORF(s) of PRRSV in vaccine preparations. Suitable ORFs include ORFs 2-7.

In another aspect of the present invention, PRRSV ORF DNA is combined with another PRRSV vaccine. Preferably the vaccine is effective at inducing an immune response prior to the addition of the PRRSV ORF1 DNA.

In yet another aspect of the present invention, a vector is provided. Vectors in accordance with the present invention have inserted therein foreign DNA (not derived from the vector) that comprises at least a portion of PRRSV ORF1 DNA. In preferred forms, the vector is a plasmid. Preferably, the portion of PRRSV ORF1 DNA will have at least 21 contiguous nucleotides from PRRSV ORF1 DNA. In some preferred forms, the portion will have at least 150 contiguous nucleotides from a sequence selected from the group consisting of sequences having at least 85% sequence identity with any one of SEQ ID Nos. 1-14, and combinations thereof. As with the composition itself, the percentage of sequence identity and length of sequence can vary as described above. In other preferred forms, the vector further comprises a second portion of PRRSV DNA. This second portion is selected from the group consisting of least 21 contiguous nucleotides from a PRRSV ORF other than ORF1, at least 21 contiguous nucleotides from ORF1, and combinations thereof. In embodiments having an additional 21 contiguous nucleotides from ORF1, these 21 nucleotides are distinct from the at least 21 nucleotides contained in the first portion of PRRSV ORF1 DNA. It is also preferred that the PRRSV DNA used to construct the vector is derived from a virulent strain of PRRSV.

Another aspect of the present invention encompasses host cells containing the plasmids of the invention. This would include the plasmids created by the introduction of the various ORF1 fragments noted above. Preferably, such a cell would contain a plasmid comprising at least 21 contiguous nucleotides from PRRSV ORF1 DNA. In other preferred forms, the cell will include a plasmid comprising at least 150 contiguous nucleotides from a sequence selected from the group consisting of sequences having at least 85% sequence identity with any one of SEQ ID Nos. 1-14, and combinations thereof. In still other preferred forms, the plasmid in the cell will comprise a second portion of PRRSV DNA selected from the group consisting of least 21 contiguous nucleotides from a PRRSV ORF other than ORF1, at least 21 contiguous nucleotides from ORF1, and combinations thereof. Preferably, the PRRSV DNA used to generate the plasmid contained in the cell is derived from a virulent strain of PRRSV.

In another aspect of the present invention, compositions of the present invention are useful in methods for the inducement of immune responses in animals as well as for the complete prevention or a reduction in the severity of conditions and symptoms caused by PRRSV infection.

The compositions of the present invention may include pharmaceutically acceptable adjuvants, carriers, and/or excipients.

As used herein, the following definitions will apply: "Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 95% "sequence identity" to a reference nucleotide sequence, it is intended that the nucleotide sequence of the given polynucleotide is identical to the reference sequence except that the given polynucleotide sequence may include up to 5 point mutations per each 100 nucleotides of the reference nucleotide sequence. In other words, in a polynucleotide having a nucleotide sequence having at least 95% identity relative to the reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 95% sequence identity to a reference amino acid sequence, it is intended that the given amino acid sequence of the polypeptide is identical to the reference sequence except that the given polypeptide sequence may include up to 5 amino acid alterations per each 100 amino acids of the reference amino acid sequence. In other words, to obtain a given polypeptide sequence having at least 95% sequence identity with a reference amino acid sequence, up to 5% of the amino acid residues in the reference sequence may be deleted or substituted with another amino acid, or a number of amino acids up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

Similarly, "sequence homology", as used herein, also refers to a method of determining the relatedness of two sequences. To determine sequence homology, two or more sequences are optimally aligned as described above, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 95% of the amino acid residues or nucleotides in the reference sequence must match or comprise a conservative substitution with another amino acid or nucleotide, or a number of amino acids or nucleotides up to 5% of the total amino acid residues or nucleotides, not including conservative substitutions, in the reference sequence may be inserted into the reference sequence.

A "conservative substitution" refers to the substitution of an amino acid residue or nucleotide with another amino acid residue or nucleotide having similar characteristics or properties including size, hydrophobicity, etc., such that the overall functionality does not change significantly.

"Isolated" means altered "by the hand of man" from its natural state., i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

"Promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

"Transfection" means the introduction of a nucleic acid, e.g., via an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a polypeptide or, in the case of antisense expression from the transferred gene, the expression of a naturally-occurring form of the protein is disrupted. Transfection may also use a chemical reagent (i.e. a lipid).

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. Vectors also include other replicons such as phages or comsmids, into which another DNA segment may be inserted so as to bring about the replication of the inserted segment. The invention is intended to include such other forms of expression vectors which serve equivalent functions and which become known in the art subsequently hereto.

"Amplification" of nucleic acids or polynucleotides is any method that results in the formation of one or more copies of a nucleic acid or polynucleotide molecule (exponential amplification) or in the formation of one or more copies of only the complement of a nucleic acid or polynucleotide molecule (linear amplification). Methods of amplification include the polymerase chain reaction (PCR) based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers. The reagents for conducting such an amplification include oligonucleotide primers, a nucleotide polymerase and nucleoside triphosphates such as, e.g., deoxyadenosine triphosphate (dATP), deoxyguanosine triphosphate (dGTP), deoxycytidine triphosphate (dCTP) and deoxythymidine triphosphate (dTTP). Other methods for amplification include amplification of a single stranded polynucleotide using a single oligonucleotide primer, the ligase chain reaction (LCR), the nucleic acid sequence based amplification (NASBA), the Q-beta-replicase method, and 3SR.

The teachings and content of all references cited herein are expressly incorporated by reference.

DETAILED DESCRIPTION OF THE PREFERRED EMBODIMENT

The following example sets forth a preferred embodiment of the present invention. It is to be understood, however, that this example is provided by way of illustration and nothing therein should be taken as a limitation upon the overall scope of the invention.

Example 1

This example provides data as to the efficacy of DNA vaccines comprising various regions of the PRRSV genome. The example began with 40 PRRSV-negative mixed sex pigs from Spring Prairie Colony, Hawley, Minn. 56549. The pigs were 3-4 weeks of age at the initiation of the study. Throughout the study, the pigs were provided food sufficient for the size, age and condition of the animals. Water was provided ad libitum.

To generate PRRSV DNA vaccines, nineteen cDNA clones were generated from the PRRS virus. Thirteen cDNA clones were generated that sequentially represent the open reading frame (ORF) 1a/1b region of the pRRSV genome. Clone A utilizes the authentic ORF1a ATG start codon. The remaining ORF1a/1b clones B through M had an ATG start codon added to their respective 5' ends. All of the above clones were respectively cloned into the DNA expression vector pVC1650. The pVC1650 vector contains the immediate early cytomegalovirus promoter and intron A to direct the expression of the various PRRSV ORFs in eukaryotic cells. The six additional cDNA clones represented the PRRSV structural protein ORFs 2, 3, 4, 5, 6 and 7. The ORF 2, 3, 4, 5, and 6 clones were also respectively cloned into the DNA expression vector pVC1650 described above. The ORF 7 gene was cloned into a similar expression vector designated WRG7020. The WRG7020 vector also contains the immediate early cytomegalovirus promoter and intron A to direct the expression of PRRSV ORF 7 in eukaryotic cells.

Two sets of vaccines were created, designated "A1-19" and "T1-19". For the A1-19 vaccines, the aforementioned clones were cloned into the Valentis, Inc. pVC1650 expression plasmid. Each plasmid construct was separately formulated with aluminum phosphate (Adju-Phos®) (Ulmer et al., Enhancement of DNA Vaccine Potency Using Conventional Aluminum Adjuvants; 18 Vaccine, 18-28 (1999) to yield 250 μg of respective ORF clone with 1000 μg calculated aluminum in a 1 ml dose. The final vaccine consisted of a separate 1 ml 1M dose of each formulated ORF clone. For the T1-19 vaccines, the aforementioned clones were cloned into the Valentis, Inc. pVC1650 expression plasmid. Each plasmid construct was separately formulated with TGV200 PINC-polymer to yield 250 μg of respective ORF clone in a 1 ml dose. The final vaccine consisted of a separate 1 ml 1M dose of each formulated ORF clone.

To generate a control, DNA vaccines consisting of cDNA clones of ORF PCV2 and the HA gene of SIV were created. Both ORFs were separately cloned into the Valentis, Inc. pVC1650 expression plasmid. Both the PCV2 ORF2 and the SIV HA gene plasmid constructs were separately formulated with aluminum phosphate (Adju-Phos®) to yield 250 μg of the respective ORF clone with 1000 μg calculated aluminum in a 1 ml dose (called A20 and A21). Additionally, both the PCV2 ORF2 and the SIV HA gene plasmid constructs were separately formulated with TGV200 PINC-polymer to yield 250 μg of each respective clone in a 1 ml dose (called T20 and T21). The final vaccine consisted of a four separate 1 ml 1M doses of each formulated clone. Table 2 shows all of the created vaccines, including the control vaccines.

TABLE 2

| Plasmid | Region of clone | Nucleotide span of clone (using Genbank U87392 as reference) |
| --- | --- | --- |
| 1 | ORF 1a | 190-1128 |
| 2 | ORF 1a | 1126-2082 |
| 3 | ORF 1a | 2082-3057 |
| 4 | ORF 1a | 3037-3990 |
| 5 | ORF 1a | 3985-4923 |
| 6 | ORF 1a | 4924-5880 |
| 7 | ORF 1a | 5863-6819 |
| 8 | ORF 1a | 6808-7659 |
| 9 | ORF 1b | 7735-8651 |
| 10 | ORF 1b | 8634-9605 |
| 11 | ORF 1b | 9588-10553 |
| 12 | ORF 1b | 10536-11318 |
| 13 | ORF 1b | 11298-12071 |
| 14 | ORF2 | NA |
| 15 | ORF3 | NA |
| 16 | ORF4 | NA |
| 17 | ORF5 | NA |
| 18 | ORF6 | NA |
| 19 | ORF7 | NA |
| 20 | ORF2 | NA |
| 21 | SIV HA | NA |

The forty pigs were divided into four groups: Group 1 was administered 19×1 ml doses of A1-A19 Adju-Phos on Days 0, 21, and 42. Group 2 was administered 19×1 ml doses of T1-T19 TGV200 on Days 0, 21, and 42. Group 3 was administered 4×1 ml respective doses of A20, A21, T20, and T21 on Days 0, 21, and 42. Group 4, the negative control, had no treatment administered at all.

On day 56 of the study, pigs in groups 1, 2, and 3 were all administered the virulent SDSU#73 strain of PRRSV. The virulent SDSU#73 strain of PRRSV was diluted 1:10 in EMEM with 4% fetal bovine serum prior to administration to the pigs. A total of 2 ml of the diluted challenge virus was delivered intranasally to the appropriate pigs with 1 ml of the diluted virus administered to each nostril. The prechallenge and postchallenge titer of the PRRSV challenge virus was $10^{4.59}$ $TCID_{50}$/ml and $10^{4.65}$ $TCID_{50}$/ml, respectively.

The pigs were bled on days 0, 21, 42 and 56 of the trial to monitor seroconversion to vaccination. The pigs were also bled on days 57, 59, 61, 63, 66 and 70 of the trial to monitor seroconversion and viremia postchallenge. Clinical observations were recorded daily from day 54-70. On day 70, pigs were necropsied and gross lung lesions were recorded as percent lung involvement due to PRRSV. Pigs were weighed prior to the study start and on Days 56 and Days 70. A summary of the protocol in this example can be seen in Table 3.

TABLE 3

| Group | Pigs/group | First vaccination (Day = 0) | Second vaccination (Day = 21) | Third vaccination (Day = 42) | Challenge (Day = 56) | Sample collection and study termination (Day = 70) |
|---|---|---|---|---|---|---|
| 1 | 10 | A1-A19 Adju-Phos | A1-A19 Adju-Phos | A1-A19 Adju-Phos | 2 ml of virulent SDSU#73 PRRSV administered intranasally. | Evaluate clinical health, rectal temperature. Evaluate animals for lung lesions at necropsy and collect designated lung tissue. |
| 2 | 10 | T1-T19 TGV200 | T1-T19 TGV200 | T1-T19 TGV200 | Same as above | Same as above |
| 3 | 10 | A20-A21 T20-T21 | A20-A21 T20-T21 | A20-A21 T20-T21 | Same as above | Same as above |
| 4 | 10 | None | None | None | None | Same as above |

In order to evaluate the results of the example, the main criteria used to determine the efficacy of the test treatments was the development of lung lesions characteristic of PRRSV. Serological response, postchallenge ADG, and rectal temperatures were evaluated as supporting criteria. The results of the example are summarized in Table 4.

TABLE 4

| Group | Group average lung scores | Percent of pigs in each group with lung consolidation scores of ≧20% | Highest group avg. temp. postchallenge (° F.) | Highest percentage of peak viremia postchallenge | Group average postchallenge ADG |
|---|---|---|---|---|---|
| 1 (A1-A19 Adju-Phos) | 19.84 | 37.5 | 105.9 | 100% | 0.16 |
| 2 (T1-T19 TGV200) | 28.42 | 70.0 | 106.0 | 100% | 0.43 |
| 3 (Chall. Ctrl) | 37.68 | 70.0 | 106.1 | 100% | 0.68 |
| (Neg. control) | 0.0A | 0.0 | 103.9 | 0% | 1.48 |

There was no seroconversion to PRRSV as determined by the IDEXX PRRS ELISA in the any of the pigs receiving three doses of the respective A1-A19 Adju-Phos or T1-T19 TGV200 DNA vaccine prototypes. After virulent PRRSV challenge, there appeared to be a more rapid increase in the ELISA S/P ratios in the Group 2 than in the Group 1 pigs. Pigs in Group 3 (unvaccinated/challenged controls) had negative S/P ratios until exposed to virulent PRRSV challenge. The strict negative control pigs in Group 4 had negative S/P ratios throughout the study. The serology results are reported in Table 5.

TABLE 5

| Group | Pig | Day 0 ELISA | Day 21 ELISA | Day 42 ELISA | Day 56 ELISA | (0 dpc) VI | Day 59 ELISA | (3 dpc) VI | Day 61 ELISA | (5 dpc) VI | Day 63 ELISA | (7 dpc) VI | Day 66 ELISA | (10 dpc) VI | Day 70 ELISA | (14 dpc) VI |
|---|---|---|---|---|---|---|---|---|---|---|---|---|---|---|---|---|
| 1 | 802 | 0.14 | −0.09 | 0.01 | 0.22 | N | 0.21 | POS | 0.97 | POS | 2.29 | POS | 2.66 | N | 2.69 | N |
| 1 | 808 | 0.00 | −0.01 | −0.01 | 0.02 | N | 0.02 | POS | 0.08 | POS | 0.66 | POS | 1.01 | N | 1.22 | N |
| 1 | 812 | −0.02 | 0.01 | −0.02 | 0.00 | N | 0.02 | N | 0.10 | POS | 0.60 | POS | 0.92 | N | 1.21 | N |
| 1 | 814 | −0.03 | 0.01 | −0.03 | 0.02 | N | 0.02 | N | 0.13 | POS | 0.54 | POS | 1.15 | N | 1.80 | N |
| 1 | 818 | 0.01 | −0.01 | 0.36 | 0.23 | N | 0.18 | POS | 0.83 | POS | 2.74 | POS | 2.97 | N | 3.24 | N |
| 1 | 826 | 0.00 | 0.00 | −0.02 | 0.01 | N | 0.01 | N | 0.10 | POS | 0.37 | POS | 0.45 | POS | ND | ND |
| 1 | 830 | −0.01 | 0.00 | 0.04 | 0.02 | N | −0.01 | POS | 0.06 | POS | 0.39 | POS | 0.97 | POS | 1.68 | N |
| 1 | 832 | −0.02 | 0.00 | −0.02 | 0.03 | N | 0.04 | N | 0.18 | POS | 0.93 | POS | 1.39 | POS | 1.71 | N |
| 1 | 839 | 0.01 | −0.05 | 0.01 | 0.08 | N | 0.06 | POS | 0.13 | POS | 0.36 | POS | 0.72 | N | 1.13 | POS |
| 1 | 842 | 0.02 | −0.01 | −0.01 | 0.17 | N | 0.19 | N | 0.92 | POS | 2.30 | POS | 2.48 | N | ND | ND |
| | Mean | 0.01 | −0.02 | 0.03 | 0.08 | | 0.07 | | 0.35 | | 1.12 | | 1.47 | | 1.84 | |
| 2 | 806 | 0.01 | 0.05 | 0.11 | 0.31 | N | 0.26 | POS | 0.58 | POS | 2.51 | POS | 3.22 | N | 3.34 | N |
| 2 | 813 | −0.02 | 0.00 | −0.03 | 0.05 | N | 0.07 | POS | 0.22 | POS | 0.83 | POS | 1.47 | POS | 1.73 | N |
| 2 | 821 | 0.00 | 0.05 | 0.04 | 0.07 | N | 0.10 | POS | 0.15 | POS | 1.12 | POS | 2.28 | N | 2.52 | N |
| 2 | 822 | −0.01 | 0.00 | −0.01 | 0.03 | N | 0.05 | POS | 0.41 | POS | 1.78 | POS | 2.37 | N | 2.01 | POS |
| 2 | 836 | −0.02 | 0.05 | 0.12 | 0.22 | N | 0.23 | POS | 0.79 | POS | 2.93 | POS | 3.52 | POS | 3.62 | N |
| 2 | 844 | 0.00 | −0.02 | 0.00 | 0.05 | N | 0.03 | POS | 0.31 | POS | 1.72 | POS | 2.33 | POS | 2.17 | N |

TABLE 5-continued

| Group | Pig | Day 0 ELISA | Day 21 ELISA | Day 42 ELISA | Day 56 ELISA | (0 dpc) VI | Day 59 ELISA | (3 dpc) VI | Day 61 ELISA | (5 dpc) VI | Day 63 ELISA | (7 dpc) VI | Day 66 ELISA | (10 dpc) VI | Day 70 ELISA | (14 dpc) VI |
|---|---|---|---|---|---|---|---|---|---|---|---|---|---|---|---|---|
| 2 | 845 | 0.04 | 0.01 | 0.06 | 0.32 | N | 0.19 | POS | 1.00 | POS | 2.80 | POS | 3.44 | N | 3.26 | N |
| 2 | 846 | −0.01 | −0.02 | −0.03 | 0.09 | N | 0.09 | N | 0.75 | POS | 2.57 | POS | 3.17 | POS | 3.06 | N |
| 2 | 847 | −0.01 | 0.01 | 0.02 | 0.04 | N | 0.02 | POS | 0.43 | POS | 2.05 | POS | 2.94 | POS | 2.96 | N |
| 2 | 849 | 0.03 | −0.02 | −0.01 | 0.11 | N | 0.08 | POS | 0.45 | POS | 1.97 | POS | 2.48 | N | 2.56 | N |
| | Mean | 0.00 | 0.01 | 0.03 | 0.13 | | 0.11 | | 0.51 | | 2.03 | | 2.72 | | 2.72 | |
| 3 | 811 | −0.03 | −0.02 | 0.02 | 0.00 | N | 0.01 | POS | 0.05 | POS | 0.55 | POS | 1.44 | POS | 1.77 | N |
| 3 | 815 | 0.00 | −0.01 | 0.06 | 0.06 | N | 0.03 | POS | 0.07 | POS | 0.57 | POS | 1.32 | POS | 1.33 | N |
| 3 | 819 | −0.01 | 0.00 | 0.04 | 0.01 | N | 0.02 | POS | 0.08 | POS | 0.25 | POS | 0.87 | POS | 1.13 | N |
| 3 | 823 | 0.00 | −0.01 | 0.03 | 0.02 | N | 0.01 | POS | 0.04 | N | 0.44 | POS | 1.13 | POS | 1.61 | N |
| 3 | 831 | 0.00 | −0.02 | 0.00 | 0.01 | N | 0.01 | POS | 0.07 | POS | 0.78 | POS | 1.48 | N | 1.75 | POS |
| 3 | 833 | −0.02 | −0.02 | 0.00 | 0.01 | N | 0.01 | POS | 0.03 | POS | 0.15 | POS | 0.43 | POS | 0.90 | N |
| 3 | 840 | 0.00 | 0.00 | 0.01 | 0.05 | N | 0.12 | POS | 0.18 | POS | 0.41 | POS | 1.30 | POS | 2.15 | POS |
| 3 | 841 | −0.02 | −0.01 | −0.02 | 0.06 | N | 0.06 | POS | 0.14 | POS | 0.71 | POS | 1.33 | POS | 1.50 | N |
| 3 | 843 | 0.00 | −0.02 | −0.01 | 0.02 | N | 0.02 | N | 0.11 | POS | 0.41 | POS | 0.84 | N | 0.80 | N |
| 3 | 848 | 0.03 | −0.02 | 0.00 | 0.05 | N | 0.05 | POS | 0.10 | POS | 0.30 | POS | 0.74 | N | 1.35 | N |
| | Mean | 0.00 | −0.02 | 0.01 | 0.03 | | 0.03 | | 0.09 | | 0.46 | | 1.09 | | 1.43 | |
| 4 | 803 | −0.03 | 0.00 | 0.04 | 0.04 | N | 0.04 | N | 0.04 | N | 0.02 | N | 0.01 | N | −0.02 | N |
| 4 | 804 | 0.01 | −0.03 | 0.02 | 0.12 | N | 0.11 | N | 0.12 | N | 0.08 | N | 0.13 | N | 0.10 | N |
| 4 | 805 | 0.03 | −0.01 | −0.03 | 0.00 | N | −0.01 | N | 0.00 | N | 0.01 | N | −0.01 | N | −0.03 | N |
| 4 | 810 | 0.01 | −0.06 | −0.03 | 0.08 | N | 0.08 | N | 0.06 | N | 0.02 | N | 0.02 | N | 0.02 | N |
| 4 | 817 | 0.03 | −0.02 | −0.15 | −0.02 | N | −0.01 | N | −0.01 | N | −0.04 | N | −0.04 | N | −0.10 | N |
| 4 | 828 | −0.02 | −0.03 | 0.04 | 0.00 | N | −0.01 | N | 0.01 | N | −0.02 | N | 0.00 | N | −0.01 | N |
| 4 | 834 | −0.01 | −0.02 | 0.03 | 0.00 | N | 0.00 | N | 0.00 | N | −0.17 | N | −0.02 | N | −0.01 | N |
| 4 | 837 | 0.00 | −0.03 | 0.01 | 0.03 | N | 0.03 | N | 0.05 | N | 0.02 | N | 0.03 | N | −0.02 | N |
| 4 | 838 | 0.00 | −0.01 | 0.00 | 0.08 | N | 0.11 | N | 0.11 | N | 0.09 | N | 0.07 | N | 0.01 | N |
| 4 | 850 | 0.04 | −0.01 | 0.03 | 0.09 | N | 0.06 | N | 0.07 | N | 0.08 | N | 0.07 | N | 0.06 | N |
| | Mean | 0.01 | −0.02 | 0.00 | 0.04 | | 0.04 | | 0.05 | | 0.01 | | 0.03 | | 0.00 | |

The pig temperatures were monitored from two days pre-challenge throughout fourteen days postchallenge. The baseline group average temperature throughout the challenge period for the Group 4 unvaccinated/unchallenged controls was 103.4° F.

The group average temperatures among all PRRSV-challenged groups were elevated at some point following challenge, however there was a temporal difference in days post challenge in which the group average temperature peaked. The group average peak temperatures in all groups challenged with PRRSV ranged from 105.9 to 106.1° F., whereas the negative controls group average peak temperature was 103.9. Group 3 showed a gradual increase in temperature postchallenge with a peak of 106.1° F. at nine days postchallenge. Groups 1 and 2 displayed a sharp increase in temperatures at two days postchallenge with peak temperatures of 105.9° F. and 105.6° F., respectively. Of note, the manner in which the postchallenge temperatures of the DNA vaccinated pigs in Group 1 and 2 rapidly increased, is similar to the manner in which PRRS KV vaccinated animals respond postchallenge. It has been observed that pigs vaccinated with experimental PRRS KV prototypes are usually "humorally-primed" (i.e. seropositive to PRRSV following vaccination). The animals vaccinated with these experimental PRRS KV prototypes also display a rapid increase in temperature soon after challenge, as was seen in this study with the DNA vaccinated pigs in Groups 1 and 2. This similarity in rapid temperature elevation following PRRSV challenge is an additional indication that the immune systems of the DNA vaccinated pigs were indeed primed to PRRSV antigen.

The Group 3 pigs displayed lung lesions characteristically found in a successful PRRSV challenge. The Group 4 pigs had no lung lesions at necropsy. The Group 1 and 2 pigs had group average lung lesions of 19.84 and 28.42, respectively. The lung scores for the individual pigs are reported in Table 6.

TABLE 6

| Group | Animal | Lung Scores |
|---|---|---|
| 1 | 802 | 2.00 |
| 1 | 808 | 0.90 |
| 1 | 812 | 55.00 |
| 1 | 814 | 0.20 |
| 1 | 818 | 1.00 |
| 1 | 826 | ND |
| 1 | 830 | 70.00 |
| 1 | 832 | 2.90 |
| 1 | 839 | 26.75 |
| 1 | 842 | ND |
| | Mean | 19.84 |
| 2 | 806 | 23.00 |
| 2 | 813 | 32.50 |
| 2 | 821 | 4.00 |
| 2 | 822 | 28.95 |
| 2 | 836 | 37.50 |
| 2 | 844 | 67.00 |
| 2 | 845 | 16.70 |
| 2 | 846 | 52.50 |
| 2 | 847 | 14.00 |
| 2 | 849 | 8.00 |
| | Mean | 28.42 |
| 3 | 811 | 2.75 |
| 3 | 815 | 33.50 |
| 3 | 819 | 51.00 |
| 3 | 823 | 72.00 |
| 3 | 831 | 75.00 |
| 3 | 833 | 15.50 |
| 3 | 840 | 39.00 |
| 3 | 841 | 37.50 |
| 3 | 843 | 9.50 |
| 3 | 848 | 41.00 |
| | Mean | 37.68 |
| 4 | 803 | 0.00 |
| 4 | 804 | 0.00 |
| 4 | 805 | 0.00 |
| 4 | 810 | 0.00 |

TABLE 6-continued

| Group | Animal | Lung Scores |
|---|---|---|
| 4 | 817 | 0.00 |
| 4 | 828 | 0.00 |
| 4 | 834 | 0.00 |
| 4 | 837 | 0.00 |
| 4 | 838 | 0.00 |
| 4 | 850 | 0.00 |
|  | Mean | 0.00 |

From these results, it is clear that DNA vaccines comprising various regions of the PRRSV genome can induce protection from virulent challenge in the respiratory model

We claim:

1. An immunogenic composition capable of inducing an immune response against PRRSV comprising:
   a vector comprising first portion of PRRSV ORF1 DNA, said first portion having at least 21 contiguous nucleotides from said PRRSV ORF1 DNA nucleotide base pair of any of sequences selected from the group consisting of any one of SEQ ID Nos. 1-14; and a suitable pharmacological carrier.

2. The immunogenic composition of claim 1, said first portion having at least 150 contiguous nucleotides from a sequence selected from the group consisting of any one of SEQ ID Nos. 1-14, and combinations thereof.

3. The immunogenic composition of claim 2, said portion being selected any of SEQ ID Nos. 1-6, 9, 10, and combinations thereof.

4. The immunogenic composition of claim 1, further comprising a second portion of DNA from PRRSV selected from the group consisting of at least 21 contiguous nucleotides from a PRRSV ORE other than ORF1, at least 21 contiguous nucleotides from a different PRRSV ORF1 portion than said first portion, and combinations thereof.

5. The immunogenic composition of claim 1, further comprising another composition effective at inducing an immune response against PRRSV infection.

6. The immunogenic composition of claim 1, said PRRSV ORF1 being derived from a virulent strain of PRRSV.

7. The immunogenic composition of claim 1, further comprising an ingredient selected from the group consisting of adjuvants, excipients, and combinations thereof.

8. A method of inducing an immune response against PRRSV in an animal susceptible to PRRSV infection, said method comprising the steps of:
   administering a composition to the animal, said composition comprising the vaccine of claim 1; and
   causing said inducement of said immune response.

9. The method of claim 8, further comprising the step of providing a second administration of said composition.

10. The method of claim 8, said portion comprising at least 150 contiguous nucleotides from a sequence selected from the group consisting of any one of SEQ ID Nos. 1-14, and combinations thereof.

11. The method of claim 10, said portion being selected from the group consisting of any of SEQ ID Nos. 1-6, 9, 10, and combinations thereof.

12. The method of claim 9, said composition further comprising a second DNA portion selected from the group consisting of at least 21 contiguous nucleotides from a PRRSV ORE other than ORF1, at least 21 contiguous nucleotides from ORF1, and combinations thereof.

13. The method of claim 9, said composition further comprising a second composition effective at inducing an immune response against PRRSV infection.

14. The method of claim 9, said composition further comprising an ingredient selected from the group consisting of adjuvants, excipients, and combinations thereof.

* * * * *